United States Patent
Yempalla et al.

(10) Patent No.: US 9,822,126 B1
(45) Date of Patent: Nov. 21, 2017

(54) SUBSTITUTED 1,2,3-TRIAZOL-1-YL-METHYL-2,3-DIHYDRO-2-METHYL-6-NITROIMIDAZO[2,1-B]OXAZOLES AS ANTI-MYCOBACTERIAL AGENTS AND A PROCESS FOR THE PREPARATION THEREOF

(71) Applicant: COUNCIL OF SCIENTIFIC & INDUSTRIAL RESEARCH, New Delhi (IN)

(72) Inventors: Kushalava Reddy Yempalla, Jammu (IN); Gurunadham Munagala, Jammu (IN); Samsher Singh, Jammu (IN); Sumit Sharma, Jammu (IN); Inshad Ali Khan, Jammu (IN); Ram Asrey Vishwakarma, Jammu (IN); Parvinder Pal Singh, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/520,799

(22) PCT Filed: Sep. 16, 2015

(86) PCT No.: PCT/IN2015/050111
§ 371 (c)(1),
(2) Date: Apr. 20, 2017

(87) PCT Pub. No.: WO2016/063298
PCT Pub. Date: Apr. 28, 2016

(30) Foreign Application Priority Data

Oct. 21, 2014 (IN) .......................... 3009/DEL/2014

(51) Int. Cl.
*C07D 498/04* (2006.01)
*A61K 31/424* (2006.01)
(52) U.S. Cl.
CPC ................ *C07D 498/04* (2013.01)
(58) Field of Classification Search
None
See application file for complete search history.

(56) References Cited

FOREIGN PATENT DOCUMENTS

| EP | 1555267 A1 | 7/2005 |
|---|---|---|
| WO | 2005/042542 A1 | 5/2005 |
| WO | 2007/043542 A1 | 4/2007 |
| WO | 2011/151320 A1 | 12/2011 |
| WO | 2015/049693 A1 | 4/2015 |

OTHER PUBLICATIONS

Heras M et al: "A New Class of Fused Imidazoles by Intramolecular Nucleophilic ipso-Substitution in 2 Alkylsulfonylimidazoles: Synthesis of 2,3-Dihydroimidazo[2,1-b][1,3]oxazoles", Synthesis, vol. 1999, No. 09, Sep. 1999, 1613-1624.

*Primary Examiner* — Alicia L Otton
(74) *Attorney, Agent, or Firm* — Maschoff Brennan

(57) ABSTRACT

The present invention relates to new generation of triazole functionality containing 6-nitro-2,3-dihydroimidazooxazole agents for general formula I, their method of preparation and their use as drugs for treatment of tuberculosis, MDR-TB and XDR-TB either alone or in combination with other anti-tubercular agents. In general formula 1, X is selected from a group $(CH_2)_n$ or a direct bond, where n is any number from 1-6, Y is selected from O, S or direct bond, $R_1$ is selected from the group consisting of H, alkyl, substituted alkyl, aryl, substituted aryl, biaryl, substituted biaryl, heterocyclic and substituted heterocyclic, wherein the substituted heterocyclic is selected from any of the following rings consisting of piperazinyl, morpholinyl, piperidyl, pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl and the substitution on aryl and biaryl is selected from the group consisting of F, Cl, Br, I, $CF_3$, $OCF_3$, $OR_{11}$, $NO_2$ and alkyl chain from C1 to C14, wherein $R_{11}$ is selected from the group consisting of H, alkyl, phenyl and substituted phenyl.

General formula I

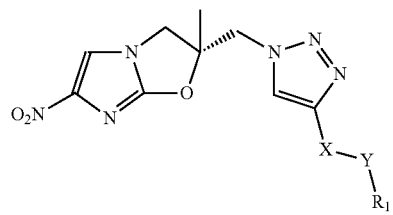

12 Claims, No Drawings

SUBSTITUTED 1,2,3-TRIAZOL-1-YL-METHYL-2,3-DIHYDRO-2-METHYL-6-NITROIMIDAZO[2,1-B]OXAZOLES AS ANTI-MYCOBACTERIAL AGENTS AND A PROCESS FOR THE PREPARATION THEREOF

FIELD OF THE INVENTION

The present invention relates to substituted 1,2,3-triazol-1-yl-methyl-2,3-dihydro-2-methyl-6-nitroimidazo[2,1-b] oxazoles as anti-mycobacterial agents. The present invention particularly relates to the compounds of 6-nitro-2,3-dihydroimidazooxazole scaffold that have been designed, synthesized and their biological evaluation result for anti-tuberculosis are presented. The present invention relates to novel compounds of general formula I, their method of preparations, and their use as drugs for treatment of tuberculosis.

BACKGROUND OF THE INVENTION

Tuberculosis remains a leading infectious cause of death worldwide and infects about one-third of the world's population. The World Health Organization (WHO) has estimated that if the present conditions remain unchanged, more than 30 million lives will be claimed by TB between 2000 and 2020. In 2012, an estimated 8.6 million people developed TB and 1.3 million died from the disease (including 320 000 deaths among HIV-positive people). TB has also been declared as a global health emergency because of the increase in secondary infections and/or co-infection in cancer and immunocompromised patients (such as those infected with human immunodeficiency virus). The existing lengthy TB therapy and emergence of multidrug resistant TB (MDR-TB) and extensively drug resistant TB (XDR-TB), [BemerMelchior, P.; Bryskier, A.; Drugeon, H. B. *J. Antimicrob. Chemother.* 2000, 46, 571; Abubaker, J.; Schraufnagel, D. *J. Am. Med. Assoc.* 2000, 283, 54; Dye. C.; Scheele, S.; Dolin, P.; Pathania, V.; Raviglione, M. C. *J. Am. Med. Assoc.* 1999, 282, 677] necessitates the development of new and potent anti-tuberculosis agents.

In this direction, we have initiated a medicinal chemistry programme on 6-nitro-2,3-dihydroimidazooxazole scaffold and discovered new potent structures (2954/DEL/2013) and in continuation, in the present invention, new generation triazole functionality containing 6-nitro-2,3-dihydroimidazooxazole is synthesized and screened for anti-TB activity.

OBJECTIVE OF THE INVENTION

The main objective of the present invention is to provide new generation triazole functionality containing 6-nitro-2,3-dihydroimidazooxazoles agents for treatment of tuberculosis.

Still another object of the present invention is to provide a process for the preparation of triazole functionality containing 6-nitro-2,3-dihydroimidazooxazoles.

Still another object of the present invention is to provide treatment against multi-drug resistant (MDR) and extensive drug resistant (XDR) tuberculosis.

SUMMARY OF THE INVENTION

The present invention relates to new generation of triazole functionality containing 6-nitro-2,3-dihydroimidazooxazole agents, their method of preparation and their use as drugs for treatment of tuberculosis.

Accordingly the present invention provides a compound having a general structure of formula I, General formula I wherein,
'X' is selected from a group $(CH_2)_n$ or a direct bond, where n is any number from 0, 1, 2 to 6,
'Y' is selected from a group O, S or direct bond,
$R_I$ is selected from the group consisting of H, alkyl, substituted alkyl, aryl, substituted aryl, biaryl, substituted biaryl, heterocyclic and substituted heterocyclic, wherein the substituted heterocyclic is selected from any of the following rings consisting of piperazinyl, morpholinyl, piperidyl, pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl and the substitution on aryl and biaryl is selected from the group consisting of F, Cl, Br, I, $CF_3$, $OCF_3$, $OR_{I1}$, $NO_2$ and alkyl chain from C1 to C14.
wherein $R_{I1}$ is selected from the group consisting of H, alkyl, phenyl, substituted phenyl.

In an embodiment of the present invention, the representative compound of general formula I comprising:
(R)-2-{[4-(4-trifluoromethoxyphenyl)-1H-1,2,3-triazol-1-yl] methyl}-2,3-dihydro-2-methyl-6-nitroimidazo[2,1-b] oxazole (compound $I_1$, Table 1)
(R)-2-{[4-(4-trifluoromethylphenyl)-1H-1,2,3-triazol-1-yl] methyl}-2,3-dihydro-2-methyl-6-nitroimidazo[2,1-b]oxazole (compound $I_2$, Table 1)
(R)-2-{[4-(4-fluorophenyl)-1H-1,2,3-triazol-1-yl]methyl}-2,3-dihydro-2-methyl-6-nitroimidazo[2,1-b]oxazole (compound $I_3$, Table 1)
(R)-2-{[4-(4-fluoro-3-methylphenyl)-1H-1,2,3-triazol-1-yl] methyl}-2,3-dihydro-2-methyl-6-nitroimidazo[2,1-b]oxazole (compound $I_4$, Table 1)
(R)-2-{[4-(2,4-difluorophenyl)-1H-1,2,3-triazol-1-yl] methyl}-2,3-dihydro-2-methyl-6-nitroimidazo[2,1-b]oxazole (compound $I_5$, Table 1)
(R)-2-{[4-(4-phenoxyphenyl)-1H-1,2,3-triazol-1-yl] methyl}-2,3-dihydro-2-methyl-6-nitroimidazo[2,1-b]oxazole (compound $I_6$, Table 1)
(R)-2-[(4-pentyl-1H-1,2,3-triazol-1-yl)methyl]-2,3-dihydro-2-methyl-6-nitroimidazo[2,1-b]oxazole (compound $I_7$, Table 1)
(R)-2-{[4-(4-trifluoromethoxyphenoxy)methyl)-1H-1,2,3-triazol-1-yl]methyl}-2,3-dihydro-2-methyl-6-nitroimidazo[2,1-b]oxazole (compound $I_8$, Table 1)
(R)-2-{[4-(4-trifluoromethylphenoxy)methyl)-1H-1,2,3-triazol-1-yl]methyl}-2,3-dihydro-2-methyl-6-nitroimidazo[2,1-b]oxazole (compound $I_9$, Table 1)
(R)-2-{[4-(3-chlorophenoxy)methyl)-1H-1,2,3-triazol-1-yl] methyl}-2,3-dihydro-2-methyl-6-nitroimidazo[2,1-b]oxazole (compound $I_{10}$, Table 1)

(R)-2-{[4-(4-bromophenoxy)methyl)-1H-1,2,3-triazol-1-yl]
   methyl}-2,3-dihydro-2-methyl-6-nitroimidazo[2,1-b]ox-
   azole (compound $I_{11}$, Table 1)
(R)-2-{[4-(4-methylphenoxy)methyl)-1H-1,2,3-triazol-1-
   yl]methyl}-2,3-dihydro-2-methyl-6-nitroimidazo[2,1-b]
   oxazole (compound $I_{12}$, Table 1)
(R)-2-{[4-(3-methylphenoxy)methyl)-1H-1,2,3-triazol-1-
   yl]methyl}-2,3-dihydro-2-methyl-6-nitroimidazo[2,1-b]
   oxazole (compound $I_{13}$, Table 1)
(R)-2-{[4-(2-methylphenoxy)methyl)-1H-1,2,3-triazol-1-
   yl]methyl}-2,3-dihydro-2-methyl-6-nitroimidazo[2,1-b]
   oxazole (compound $I_{14}$, Table 1)
(R)-2-{[4-(4-ethylphenoxy)methyl)-1H-1,2,3-triazol-1-yl]
   methyl}-2,3-dihydro-2-methyl-6-nitroimidazo[2,1-b]ox-
   azole (compound $I_{15}$, Table 1)
(R)-2-{[4-(3-fluorophenoxy)methyl)-1H-1,2,3-triazol-1-yl]
   methyl}-2,3-dihydro-2-methyl-6-nitroimidazo[2,1-b]ox-
   azole (compound $I_{16}$, Table 1)
(R)-2-{[4-(2-fluorophenoxy)methyl)-1H-1,2,3-triazol-1-yl]
   methyl}-2,3-dihydro-2-methyl-6-nitroimidazo[2,1-b]ox-
   azole (compound $I_{17}$, Table 1)
(R)-2-{[4-(4-isopropylphenoxy)methyl)-1H-1,2,3-triazol-1-
   yl]methyl}-2,3-dihydro-2-methyl-6-nitroimidazo[2,1-b]
   oxazole (compound $I_{18}$, Table 1)
(R)-2-methyl-6-nitro-2-((4-((pyridin-2-yloxy)methyl)-1H-
   1,2,3-triazol-1-yl)methyl)-2,3-dihydroimidazo[2,1-b]ox-
   azole (compound $I_{19}$, Table 1)
(R)-2-methyl-6-nitro-2-((4-((p-tolylthio)methyl)-1H-1,2,3-
   triazol-1-yl)methyl)-2,3-dihydroimidazo[2,1-b]oxazole
   (compound $I_{20}$, Table 1)
(R)-2-methyl-6-nitro-2-((4-(2-(p-tolyloxy)ethyl)-1H-1,2,3-
   triazol-1-yl)methyl)-2,3-dihydroimidazo[2,1-b]oxazole
   (compound $I_{21}$, Table 1)
(R)-2-methyl-2-((4-(morpholinomethyl)-1H-1,2,3-triazol-1-
   yl)methyl)-6-nitro-2,3-dihydroimidazo[2,1-b]oxazole
   (compound $I_{22}$, Table 1)

In an embodiment of the invention wherein the compound of general formula I, for use in treatment of tuberculosis.

In yet another embodiment of the invention of general formula I, wherein said compound exhibits an in-vitro anti-tuberculosis activity against $H_{37}$Rv *Mycobacterium tuberculosis*, MDR-TB (resistant to isoniazid and rifampicin) with MIC values in the range of 0.12 to 32 µg/ml.

In still another embodiment of the invention of general formula I, wherein said compound exhibits an in vitro anti-tuberculosis activity against XDR-TB (resistant to isoniazid, rifampicin, amikacin and moxifloxacin) with MIC values in the range of 0.12 to 32 (µg/ml).

In another embodiment of the invention of general formula I, wherein said compound does not exhibit any cytotoxicity up to 40 µg/ml in macrophage J774 cell line.

The compound of formula I exhibits an in vitro anti-tuberculosis activity against replicating and non-replicating stages of *Mycobacterium tuberculosis* with MIC values in the range of 0.12 to 32 µg/ml.

The compound of formula I exhibits an in vitro anti-tuberculosis activity against XDR *Mycobacterium tuberculosis* (resistant to isoniazid, rifampicin, amikacin and moxifloxacin), MDR-TB (resistant to isoniazid and rifampicin) with MIC values in the range of 0.12 to 32 µg/ml and the compound does not exhibit any cytotoxicity up to 40 µg/ml in macrophage J774 cell line.

The present invention also provides a process for preparation of the compound of formula I wherein the said process comprising the steps:

i) reacting a compound of formula 8 in an organic solvent selected from group consisting of toluene, acetonitrile, DMF, dichloroethane or any combination thereof in the presence of an azide source selected from sodiumazide, trimethylsilylazide and tetrabutyl ammonium bromide at a temperature in the range of 25° C. to 80° C. for a period ranging between 1 h to 3 h to obtain the desired compound of formula 9.

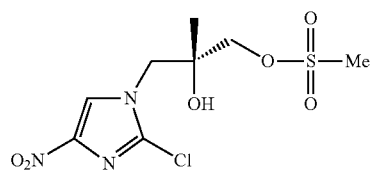

8

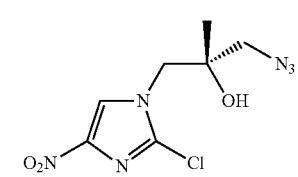

9 ii) reacting the compound of formula 9 with a base selected from a group consisting of sodium hydride, cesium carbonate, potassium carbonate or any combination thereof in an organic solvent selected from a group consisting of toluene, acetonitrile, DMF, tetrahydrofuran or any combination thereof in the presence of at a temperature in the range of 10° C.-25° C. for a period of 1 h to 12 h to obtain a desired compound of formula 10.

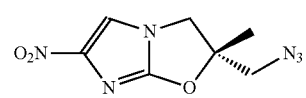

10 iii) reacting the compound of formula 10 with a compound of formula selected from the group consisting of formula 13(a-k) or 14(a-g) or 15(a-d) in 1:1 tert-BuOH/H$_2$O mixture in the presence of sodiumascorbate and CuSO$_4$ at a temperature in the range of 10° C. to 25° C. for a period of 1 h to 12 h to obtain the desired compound of formula I.

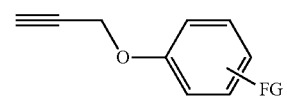

13(a-k)

13a; FG = 4-OCF$_3$
13b; FG = 4-CF$_3$
13c; FG = 4-Cl
13d; FG = 2-Br
13e; FG = 4-Me
13f; FG = 3-Me
13g; FG = 2-Me
13h; FG = 4-Et
13i; FG = 3-F
13j; FG = 2-F
13k; FG = 4-iso-propyl 14 (a-g)

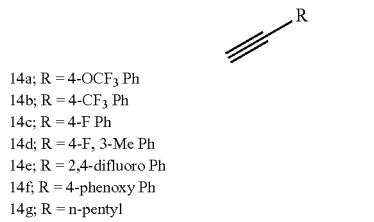

14a; R = 4-OCF₃ Ph
14b; R = 4-CF₃ Ph
14c; R = 4-F Ph
14d; R = 4-F, 3-Me Ph
14e; R = 2,4-difluoro Ph
14f; R = 4-phenoxy Ph
14g; R = n-pentyl 15 (a-d)

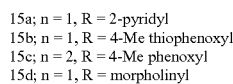

15a; n = 1, R = 2-pyridyl
15b; n = 1, R = 4-Me thiophenoxyl
15c; n = 2, R = 4-Me phenoxyl
15d; n = 1, R = morpholinyl

LIST OF ABBREVIATIONS

ATCC: american type culture collection
AcOH: acetic acid
CFU: colony forming units
DMAP: 4-dimethylaminopyridine
DCM: dichloromethane
d: doublet
dd: doublet of doublet
Et: ethyl
ESI: electron spray ionisation
FCS: fetal calf serum
$H_{37}Rv$: a well characterised virulent strain of *Mycobacterium tuberculosis*
h: hours
$IC_{50}$: half maximal inhibitory concentration
J: coupling constant
MIC: minimum inhibitory concentration
MS: mass spectrometry
ml: milliliter
MHz: mega hertz
m: multiplet
MDR-TB: Multi drug resistant tuberculosis
Me: methyl
min: minutes
m/z: mass to charge ratio
MTB: *Mycobacterium tuberculosis*
NMP: N-methylpyrrolidinone
$Rif^R$: rifampicin resistant tuberculosis
RPMI: rosewell park memorial institute medium
$R_f$: retention factor
s: singlet
TFA: trifluoroacetic acid
TLC: thin layer chromatography
TB: Tuberculosis
TDR-TB: Total drug resistant tuberculosis
t: triplet
tert: tertiary
WHO: world health organization
XDR-TB: Extensive drug resistant tuberculosis
μg: microgram
¹H NMR: proton nuclear magnetic resonance

DETAILED DESCRIPTION OF THE INVENTION

The present invention relates to new generation of triazole functionality containing 6-nitro-2,3-dihydroimidazooxazole agents, their method of preparation and their use as drugs for treatment of tuberculosis.

The present invention describes a compound having general structure of formula I General formula I

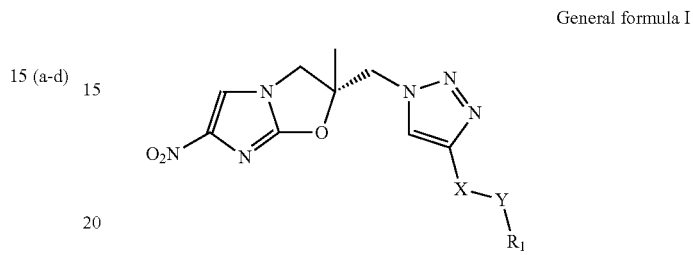

wherein
'X' is selected from a group $(CH_2)_n$ or a direct bond, where n is any number from 0, 1, 2 to 6,
'Y' is selected from a group O, S or direct bond,
RI is selected from the group consisting of H, alkyl, substituted alkyl, aryl, substituted aryl, biaryl, substituted biaryl, heterocyclic and substituted heterocyclic, wherein the substituted heterocyclic is selected from any of the following rings consisting of piperazinyl, morpholinyl, piperidyl, pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl and the substitution on aryl and biaryl is selected from the group consisting of F, Cl, Br, I, CF3, OCF3, ORI1, NO2 and alkyl chain from C1 to C14.
wherein $R_{I1}$ is selected from the group consisting of H, alkyl, phenyl, substituted phenyl.

The most preferred compounds of general formula I are:
(R)-2-{[4-(4-trifluoromethoxyphenyl)-1H-1,2,3-triazol-1-yl]methyl}-2,3-dihydro-2-methyl-6-nitroimidazo[2,1-b]oxazole (compound I₁, Table 1)
(R)-2-{[4-(4-trifluoromethylphenyl)-1H-1,2,3-triazol-1-yl]methyl}-2,3-dihydro-2-methyl-6-nitroimidazo[2,1-b]oxazole (compound I₂, Table 1)
(R)-2-{[4-(4-fluorophenyl)-1H-1,2,3-triazol-1-yl]methyl}-2,3-dihydro-2-methyl-6-nitroimidazo[2,1-b]oxazole (compound I₃, Table 1)
(R)-2-{[4-(4-fluoro-3-methylphenyl)-1H-1,2,3-triazol-1-yl]methyl}-2,3-dihydro-2-methyl-6-nitroimidazo[2,1-b]oxazole (compound I₄, Table 1)
(R)-2-{[4-(2,4-difluorophenyl)-1H-1,2,3-triazol-1-yl]methyl}-2,3-dihydro-2-methyl-6-nitroimidazo[2,1-b]oxazole (compound I₅, Table 1)
(R)-2-{[4-(4-phenoxyphenyl)-1H-1,2,3-triazol-1-yl]methyl}-2,3-dihydro-2-methyl-6-nitroimidazo[2,1-b]oxazole (compound I₆, Table 1)
(R)-2-[(4-pentyl-1H-1,2,3-triazol-1-yl)methyl]-2,3-dihydro-2-methyl-6-nitroimidazo[2,1-b]oxazole (compound I₇, Table 1)
(R)-2-{[4-(4-trifluoromethoxyphenoxy)methyl)-1H-1,2,3-triazol-1-yl]methyl}-2,3-dihydro-2-methyl-6-nitroimidazo[2,1-b]oxazole (compound I₈, Table 1)

(R)-2-{[4-(4-trifluoromethylphenoxy)methyl)-1H-1,2,3-tri-azol-1-yl]methyl}-2,3-dihydro-2-methyl-6-nitroimidazo[2,1-b]oxazole (compound $I_9$, Table 1)

(R)-2-{[4-(3-chlorophenoxy)methyl)-1H-1,2,3-triazol-1-yl]methyl}-2,3-dihydro-2-methyl-6-nitroimidazo[2,1-b]oxazole (compound $I_{10}$, Table 1)

(R)-2-{[4-(4-bromophenoxy)methyl)-1H-1,2,3-triazol-1-yl]methyl}-2,3-dihydro-2-methyl-6-nitroimidazo[2,1-b]oxazole (compound $I_{11}$, Table 1)

(R)-2-{[4-(4-methylphenoxy)methyl)-1H-1,2,3-triazol-1-yl]methyl}-2,3-dihydro-2-methyl-6-nitroimidazo[2,1-b]oxazole (compound $I_{12}$, Table 1)

(R)-2-{[4-(3-methylphenoxy)methyl)-1H-1,2,3-triazol-1-yl]methyl}-2,3-dihydro-2-methyl-6-nitroimidazo[2,1-b]oxazole (compound $I_{13}$, Table 1)

(R)-2-{[4-(2-methylphenoxy)methyl)-1H-1,2,3-triazol-1-yl]methyl}-2,3-dihydro-2-methyl-6-nitroimidazo[2,1-b]oxazole (compound $I_{14}$, Table 1)

(R)-2-{[4-(4-ethylphenoxy)methyl)-1H-1,2,3-triazol-1-yl]methyl}-2,3-dihydro-2-methyl-6-nitroimidazo[2,1-b]oxazole (compound $I_{15}$, Table 1)

(R)-2-{[4-(3-fluorophenoxy)methyl)-1H-1,2,3-triazol-1-yl]methyl}-2,3-dihydro-2-methyl-6-nitroimidazo[2,1-b]oxazole (compound $I_{16}$, Table 1)

(R)-2-{[4-(2-fluorophenoxy)methyl)-1H-1,2,3-triazol-1-yl]methyl}-2,3-dihydro-2-methyl-6-nitroimidazo[2,1-b]oxazole (compound $I_{17}$, Table 1)

(R)-2-{[4-(4-isopropylphenoxy)methyl)-1H-1,2,3-triazol-1-yl]methyl}-2,3-dihydro-2-methyl-6-nitroimidazo[2,1-b]oxazole (compound $I_{18}$, Table 1)

(R)-2-methyl-6-nitro-2-((4-((pyridin-2-yloxy)methyl)-1H-1,2,3-triazol-1-yl)methyl)-2,3-dihydroimidazo[2,1-b]oxazole (compound $I_{19}$, Table 1)

(R)-2-methyl-6-nitro-2-((4-((p-tolylthio)methyl)-1H-1,2,3-triazol-1-yl)methyl)-2,3-dihydroimidazo[2,1-b]oxazole (compound $I_{20}$, Table 1)

(R)-2-methyl-6-nitro-2-((4-(2-(p-tolyloxy)ethyl)-1H-1,2,3-triazol-1-yl)methyl)-2,3-dihydroimidazo[2,1-b]oxazole (compound $I_{21}$, Table 1)

(R)-2-methyl-2-((4-(morpholinomethyl)-1H-1,2,3-triazol-1-yl)methyl)-6-nitro-2,3-dihydroimidazo[2,1-b]oxazole (compound $I_{22}$, Table 1)

The compounds of general formula I, are useful in treatment of tuberculosis.

The compound of general formula I, exhibits an in vitro anti-tuberculosis activity against $H_{37}Rv$ *Mycobacterium tuberculosis*, MDR-TB (resistant to isoniazid and rifampicin) with MIC values in the range of 0.12 to 32 μg/ml.

The compound of general formula I, exhibits an in vitro anti-tuberculosis activity against XDR-TB (resistant to isoniazid, rifampicin, amikacin and moxifloxacin) with MIC values in the range of 0.12 to 32 (μg/ml).

The compound of general formula I does not exhibit any cytotoxicity up to 40 μg/ml in macrophage J774 cell line.

An embodiment of the invention; provides a process for the preparation of a compound of formula 9, wherein the process step comprising of the reaction of compound of formula 8 in an organic solvent selected from toluene, acetonitrile, DMF, dichloroethane or any combination thereof in the presence of azide source selected from sodiumazide, trimethylsilylazide, tetrabutyl ammonium bromide or any combination thereof at a temperature in the range of 25° C. to 80° C. for a period of 1 h to 3 h to obtain the desired compound of formula 9.

In another embodiment of the invention a process for the preparation of the compound of formula 10, wherein the process step comprising of the reaction of compound of formula 9 in an organic solvent selected from toluene, acetonitrile, DMF, tetrahydrofuran or any combination thereof in the presence of base selected from sodium hydride, cesium carbonate, potassium carbonate or any combination thereof at a temperature in the range of 10° C. to 25° C. for a period of 1 h to 12 h to obtain the desired compound of formula 10.

In another embodiment of the invention, a process for the preparation of the compound of general formula I, wherein the process step comprising the reacting compound of formula 10 with a compound of formula selected from the group consisting of formula 13 or 14 or 15 in 1:1 tert-BuOH/$H_2O$ mixture in the presence of sodium ascorbate and $CuSO_4$ at a temperature in the range of 10° C. to 25° C. for a period of 1 h to 12 h to obtain the desired compound of general formula I.

The present invention discloses process for synthesis of the fragments A and B which in turn can be used for synthesis of compounds of general formula I. The entire synthesis of compound I is illustrated by Reaction Schemes 1 to 4 as given below:—

Scheme 1: The Synthesis of the fragment A (compound of formula 10)

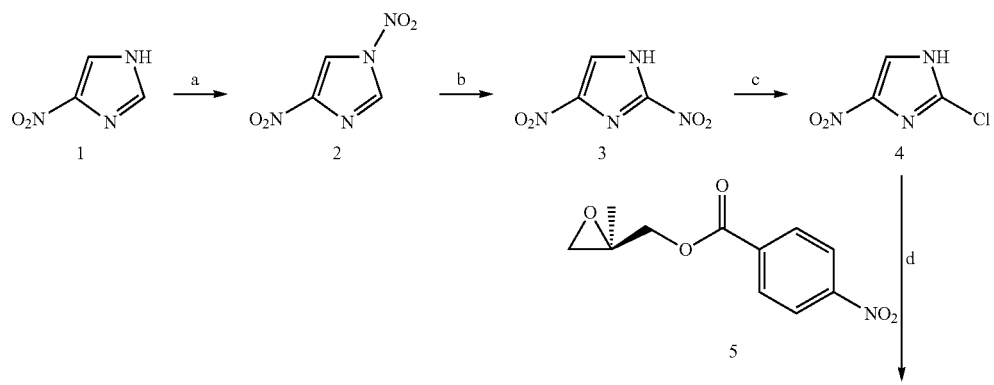

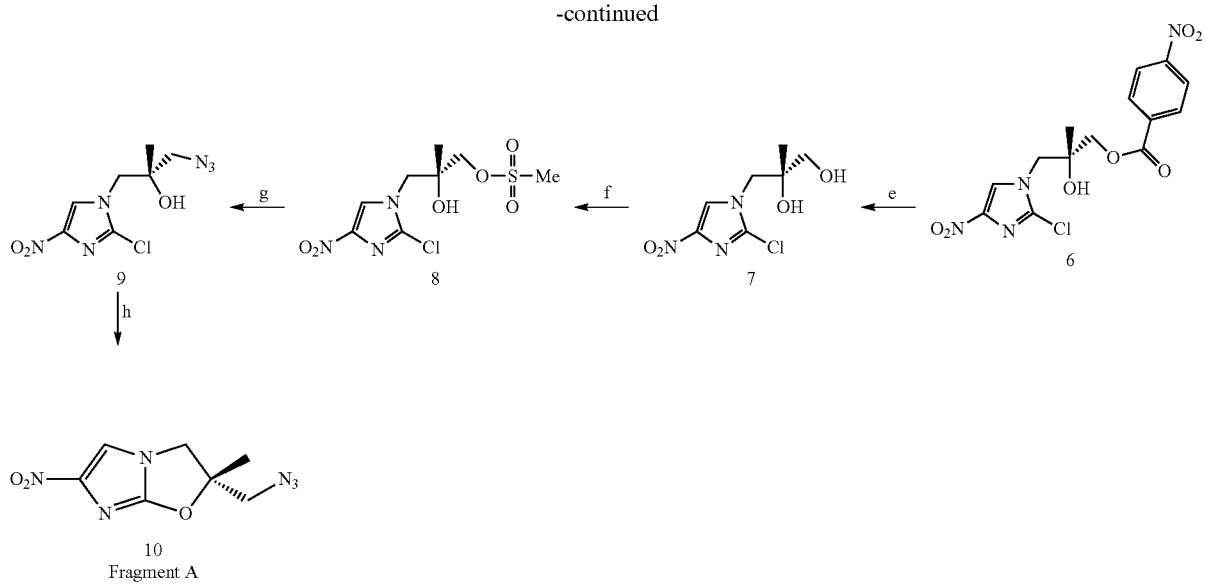

10
Fragment A

Scheme1: Reagents and conditions:
a) HNO₃, ACOH, AC₂O, 5° C., 2 h, and then at rt, 12 h;
b) chloro benzene, 120-125° C., 50 h;
c) con HCl, 90-95° C., 12 h;
d) Et₃N, AcOEt, 60-65° C., 6 h;
e) K₂CO₃, MeOH, rt, 2 h;
f) MsCl, pyridine, <15° C., 2 h;
g) NaN₃, DMF, TBAB, 80° C. 3 h;
h) Cs₂CO₃, DMF, <15° C.-rt, 12 h.

Scheme 2: The synthesis of the fragment B {compounds of formula 13(a-k)}

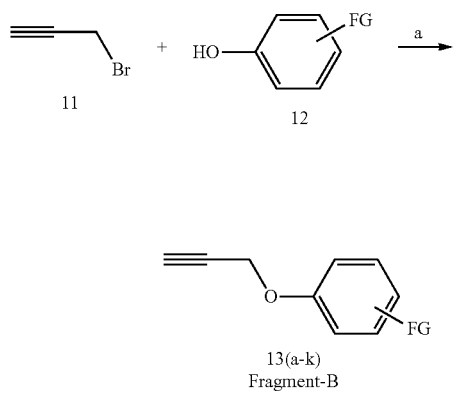

13(a-k)
Fragment-B

13a; FG = 4-OCF₃
13b; FG = 4-CF₃
13c; FG = 4-Cl
13d; FG = 2-Br
13e; FG = 4-Me
13f; FG = 3-Me
13g; FG = 2-Me
13h; FG = 4-Et
13i; FG = 3-F
13j; FG = 2-F
13k; FG = 4-iso-propyl
Scheme 2: Reagents and Conditions:
a) K₂CO₃, ACN, rt, 12 h.

Scheme 3: The synthesis of representing compounds (I₁ to I₇) of general formula I by coupling of fragment A (compound of formula 10) with fragment C (compound of formula 14)

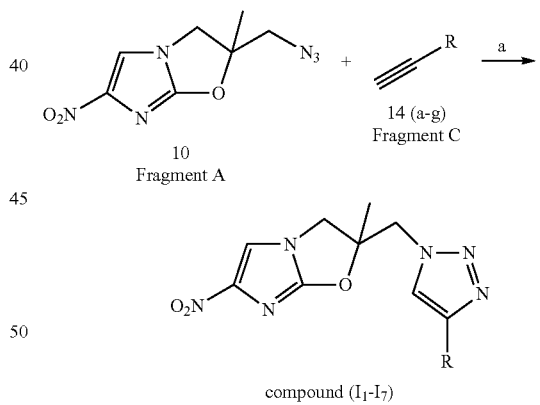

compound (I₁-I₇)

14a; R = 4-OCF₃ Ph
14b; R = 4-CF₃ Ph
14c; R = 4-F Ph
14d; R = 4-F, 3-Me Ph
14e; R = 2, 4-difluoro Ph
14f; R = 4-phenoxy Ph
14g; R = n-pentyl
I₁; R = 4-OCF₃ Ph
I₂; R = 4-CF₃ Ph
I₃; R = 4-F Ph
I₄; R = 4-F, 3-Me Ph
I₅; R = 2, 4-difluoro Ph
I₆; R = 4-phenoxy Ph
I₇; R = n-pentyl Scheme 3: Reagents and Conditions:
a) CuSO₄, ᵗBuOH, H₂O, Sodium Ascorbate, RT, 12 h:

Scheme 4: The synthesis of the representing compounds (I₈ to I₁₈) of general formula I by coupling of fragment A (compound of formula 10) with fragment B {compounds of formula 13(a-k)}

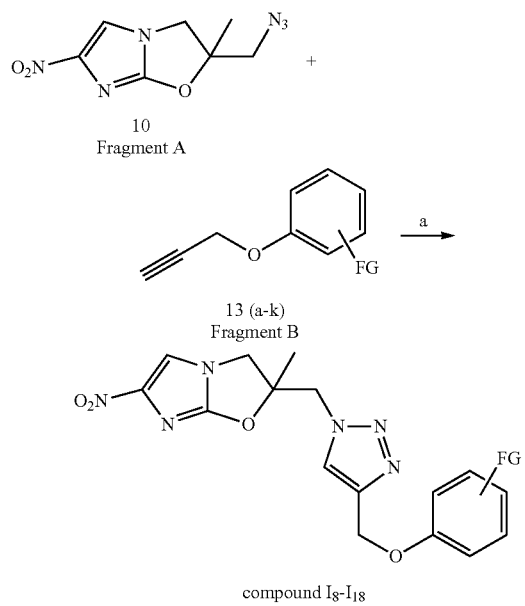

10
Fragment A 13 (a-k)
Fragment B compound I₈-I₁₈

13a; FG = 4-OCF₃
13b; FG = 4-CF₃
13c; FG = 4-Cl
13d; FG = 2-Br
13e; FG = 4-Me
13f; FG = 3-Me
13g; FG = 2-Me
13h; FG = 4-Et
13i; FG = 3-F
13j; FG = 2-F
13k; FG = 4-iso-propyl
I₈; FG = 4-OCF₃
I₉; FG = 4-CF₃
I₁₀; FG = 4-Cl
I₁₁; FG = 4-Br
I₁₂; FG = 4-Me
I₁₃; FG = 3-Me
I₁₄; FG = 2-Me
I₁₅; FG = 4-Et
I₁₆; FG = 3-F
I₁₇; FG = 2-F
I₁₈; FG = 4-iso-propyl
Scheme 4: Reagents and conditions:
a) CuSO₄, ᵗBuOH, H₂O, Sodium Ascorbate, RT, 12h:

Scheme 5: The synthesis of the representing compounds (I₉ to I₂₂) of general formula I by coupling of fragment A (compound of formula 10) with a compound of formula 15 (a-d)

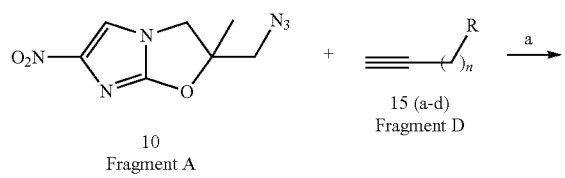

10
Fragment A 15 (a-d)
Fragment D

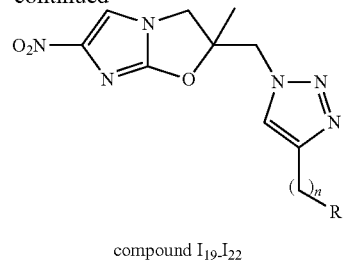

compound I₁₉-I₂₂

15a; n = 1, R = 2-pyridyl
15b; n = 1, R = 4-Me thiophenoxyl
15c; n = 2, R = 4-Me phenoxyl
15d; n = 1, R = morpholinyl
I₁₉; n = 1, R = 2-pyridyl
I₂₀; n = 1, R = 4-Me thiophenoxyl
I₂₁; n = 2, R = 4-Me phenoxyl
I₂₂; n = 1, R = morpholinyl
Scheme 5: Reagents and conditions:
a) CuSO₄, ᵗBuOH, H₂O, Sodium Ascorbate, RT, 12 h:

EXAMPLES

Synthesis of Compounds:

The following examples are given by way of illustrating the present invention and should not be construed to limit the scope of the invention:

R)-3-(2-Chloro-4-nitro-1H-imidazol-1-yl)-2-hydroxy-2-methylpropylmethanesulfonate (8)

The synthesis of compound 8 was successfully synthesized from a starting material 4-Nitroimidiazole 1 as shown in scheme 1 by following known procedure (Sasaki, H.; Haraguchi, Y.; Itotani, M.; Kuroda, H.; Hashizume, H.; Tomishige, T.; Kawasaki, M.; Matsumoto, M.; Komatsu, M.; Tsubouchi, H. *J. Med. Chem.* 2006, 49, 7854.

Example 1

(R)-1-Azido-3-(2-chloro-4-nitro-1H-imidazol-1-yl)-2-methylpropan-2-ol (9)

To a solution of (R)-3-(2-Chloro-4-nitro-1H-imidazol-1-yl)-2-hydroxy-2-methylpropyl methanesulfonate (8) (10 mmol) in DMF (20 mL) was added sodium azide (30 mmol) and tetrabutyl ammonium bromide (1 mmol). After the solution was stirred at 80° C. for 3 h, the reaction mixture was extracted with ethyl acetate twice, and the combined organic layer was washed with brine, dried over sodium sulphate, and filtered. The filtrate was concentrated under reduced pressure. The residue was purified by silica gel column chromatography in 5% DCM/Ethyl acetate to give the compound 9 as yellow colour solid. The compound 9 is also prepared using the process as described above using different solvents such as toluene, acetonitrile or dichloroethane at 60-80° C. for a period of 2-4 hr as given in the following table.

| Reactant | Solvent | Temp ° C. | Time | Reagents | Product |
|---|---|---|---|---|---|
| (R)-3-(2-Chloro-4-nitro-1H-imidazol-1-yl)-2-hydroxy-2-methylpropyl methanesulfonate (8) | Toluene | 60 | 2 | Sodium azide | (R)-1-Azido-3-(2-chloro-4-nitro-1H-imidazol-1-yl)-2-methylpropan-2-ol (9) |
| (R)-3-(2-Chloro-4-nitro-1H-imidazol-1-yl)-2-hydroxy-2-methylpropyl methanesulfonate (8) | Acetonitrile | 60 | 4 | Trimethylsilyl azide | (R)-1-Azido-3-(2-chloro-4-nitro-1H-imidazol-1-yl)-2-methylpropan-2-ol (9) |
| (R)-3-(2-Chloro-4-nitro-1H-imidazol-1-yl)-2-hydroxy-2-methylpropyl methanesulfonate (8) | dichloroethane | 80 | 2 | Sodium azide | (R)-1-Azido-3-(2-chloro-4-nitro-1H-imidazol-1-yl)-2-methylpropan-2-ol (9) |

Example 2

(R)-2-(Azidomethyl)-2-methyl-6-nitro-2,3-dihydroimidazo[2,1-b]oxazole (10)

To a solution of (R)-1-Azido-3-(2-chloro-4-nitro-1H-imidazol-1-yl)-2-methylpropan-2-ol 9)(10 mmol) in DMF (20 mL) was added cesium carbonate (30 mmol) at below 15° C. portion wise, After the solution was stirred for 12 h at 25° C., The reaction mixture was poured into the ice water and extracted with ethyl acetate twice, and the combined organic layer was washed with brine, dried over sodium sulphate, and filtered. The filtrate was concentrated under reduced pressure. The residue was purified by silica gel column chromatography to give the compound 10 as yellow colour solid.

The reaction is also carried out by using the different solvent such as toluene, acetonitrile or tetrahydrofurane at 25° C. for a period of 6-12 hr. to produce the compound 10.

| Reactant | Solvent | Tem. ° C. | Time | Reagents | Product |
|---|---|---|---|---|---|
| (R)-1-Azido-3-(2-chloro-4-nitro-1H-imidazol-1-yl)-2-methylpropan-2-ol (9) | DMF | 25 | 6 | Sodium hydride | (R)-2-(Azidomethyl)-2-methyl-6-nitro-2,3-dihydroimidazo [2,1-b] oxazole (10) |
| (R)-1-Azido-3-(2-chloro-4-nitro-1H-imidazol-1-yl)-2-methylpropan-2-ol (9) | Toluene | 25 | 6 | Sodium hydride | (R)-2-(Azidomethyl)-2-methyl-6-nitro-2,3-dihydroimidazo [2,1-b] oxazole (10) |
| (R)-1-Azido-3-(2-chloro-4-nitro-1H-imidazol-1-yl)-2-methylpropan-2-ol (9) | Acetonitrile | 25 | 12 | Potassium carbonate | (R)-2-(Azidomethyl)-2-methyl-6-nitro-2,3-dihydroimidazo [2,1-b] oxazole (10) |
| (R)-1-Azido-3-(2-chloro-4-nitro-1H-imidazol-1-yl)-2-methylpropan-2-ol (9) | tetrahydrofuran | 25 | 12 | Sodium carbonate | (R)-2-(Azidomethyl)-2-methyl-6-nitro-2,3-dihydroimidazo [2,1-b] oxazole (10) |

Example 3

General Procedure for the Preparation of Compounds ($I_1$ to $I_{22}$):

(R)-2-(Azidomethyl)-2-methyl-6-nitro-2,3-dihydroimidazo[2,1-b]oxazole (10) (1 mmol) and 13 (a-k) or 14 (a-g) or 15 (a-d) suspended in 6 mL of a 1:1 tert-BuOH/H2O mixture. While the mixture was being stirred, sodium ascorbate (0.1 mmol) was added, followed by $CuSO_4$ pentahydrate (0.02 mmol). Left stirring for 12 h at 25° C., after which time it was diluted with water, and the solid was filtered off. The crude was purified by silica gel column chromatography to give the compounds $I_1$ to $I_{22}$.

(R)-2-Methyl-6-nitro-2-((4-(4-(trifluoromethoxy)phenyl)-1H-1,2,3-triazol-1-yl)methyl)-2,3-dihydroimidazo[2,1-b]oxazole ($I_1$, Table 1, Scheme 3)

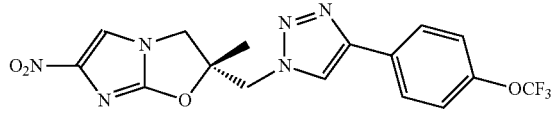 [SMILES: C[C@]1(Cn2cc(-c3ccc(OC(F)(F)F)cc3)nn2)Cn2cc([N+](=O)[O-])nc2O1]

TLC (EtOAc:DCM 1:9): $R_f$=0.3; $^1$H NMR (400 MHz, Acetone) δ 8.50 (s, 2H), 8.01 (t, J=4.5 Hz, 7H), 7.39 (d, J=8.0 Hz, 5H), 5.10 (q, J=14.9 Hz, 6H), 4.66 (d, J=11.2 Hz, 3H), 4.42 (d, J=11.2 Hz, 3H), 1.79 (s, 7H); MS (ESI+): m\z 410.0950.

(R)-2-Methyl-6-nitro-2-((4-(4-(trifluoromethyl)phenyl)-1H-1,2,3-triazol-1-yl)methyl)-2,3-dihydroimidazo[2,1-b]oxazole ($I_2$, Table 1, Scheme 3)

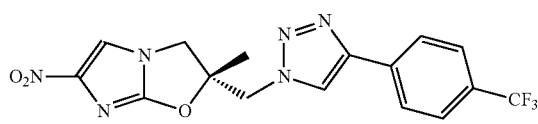 [SMILES: C[C@]1(Cn2cc(-c3ccc(C(F)(F)F)cc3)nn2)Cn2cc([N+](=O)[O-])nc2O1]

TLC (EtOAc:DCM 1:9): R$_f$=0.45; $^1$H NMR (400 MHz, DMSO) δ 8.74 (s, 1H), 8.07 (t, J=4.0 Hz, 3H), 7.81 (d, J=8.3 Hz, 2H), 5.05 (d, J=14.8 Hz, 1H), 4.98 (d, J=14.8 Hz, 1H), 4.44 (d, J=11.3 Hz, 1H), 4.26 (d, J=11.3 Hz, 1H), 1.63 (s, 3H); MS (ESI+): m\z 394.1001.

(R)-2-((4-(4-Fluorophenyl)-1H-1,2,3-triazol-1-yl)methyl)-2-methyl-6nitro-2,3-dihydro imidazo[2,1-b]oxazole (I$_3$, Table 1, Scheme 3)

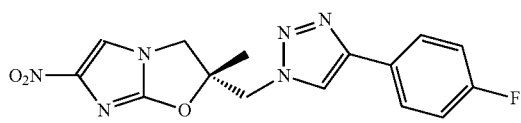 [SMILES: C[C@]1(Cn2cc(-c3ccc(F)cc3)nn2)Cn2cc([N+](=O)[O-])nc2O1]

TLC (EtOAc:DCM 1:9): R$_f$=0.35; $^1$H NMR (400 MHz, DMSO) δ 8.54 (s, 1H), 8.05 (s, 1H), 7.87 (dd, J=8.7, 5.5 Hz, 2H), 7.28 (t, J=8.9 Hz, 2H), 5.01 (d, J=14.8 Hz, 1H), 4.95 (d, J=14.8 Hz, 1H), 4.42 (d, J=11.3 Hz, 1H), 4.24 (d, J=11.2 Hz, 1H), 1.63 (s, 3H); MS (ESI+): m\z 344.1033.

(R)-2-((4-(4-Fluoro-3-methylphenyl)-1H-1,2,3-triazol-1-yl)methyl)-2-methyl-6-nitro-2,3-dihydroimidazo[2,1-b]oxazole (I$_4$, Table 1, Scheme 3)

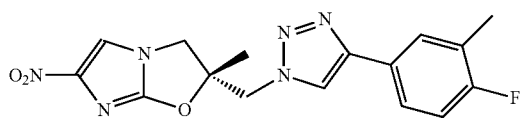 [SMILES: Cc1cc(-c2cn(C[C@@]3(C)Cn4cc([N+](=O)[O-])nc4O3)nn2)ccc1F]

TLC (EtOAc:DCM 1:9): R$_f$=0.5; $^1$H NMR (400 MHz, DMSO) δ 8.47 (s, 1H), 8.02 (s, 1H), 7.72 (d, J=7.0 Hz, 1H), 7.69-7.60 (m, 1H), 7.19 (t, J=9.1 Hz, 1H), 5.00 (d, J=14.8 Hz, 1H), 4.93 (d, J=14.8 Hz, 1H), 4.41 (d, J=11.3 Hz, 1H), 4.23 (d, J=11.3 Hz, 1H), 2.27 (s, 3H), 1.63 (s, 3H); MS (ESI+): m\z 358.1190.

(R)-2-((4-(2,4-Difluorophenyl)-1H-1,2,3-triazol-1-yl)methyl)-2-methyl-6-nitro-2,3-dihydroimidazo[2,1-b]oxazole (I$_5$, Table 1, Scheme 3)

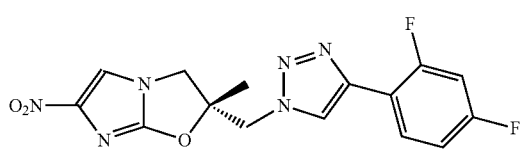 [SMILES: C[C@]1(Cn2cc(-c3ccc(F)cc3F)nn2)Cn2cc([N+](=O)[O-])nc2O1]

TLC (EtOAc:DCM 1:9): R$_f$=0.25; $^1$H NMR (500 MHz, Acetone) δ 8.35 (d, J=3.6 Hz, 2H), 8.21 (dd, J=15.5, 8.8 Hz, 2H), 7.81 (s, 2H), 7.20-7.11 (m, 4H), 5.15 (q, J=14.9 Hz, 6H), 4.68 (d, J=11.1 Hz, 3H), 4.43 (d, J=11.1 Hz, 3H), 1.79 (s, 8H); MS (ESI+): m\z 362.0939.

(R)-2-Methyl-6-nitro-2-((4-(4-phenoxyphenyl)-1H-1,2,3-triazol-1-yl)methyl)-2,3-dihydroimidazo[2,1-b]oxazole (I$_6$, Table 1, Scheme 3)

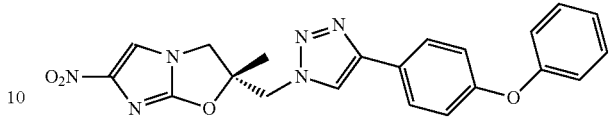

TLC (EtOAc:DCM 1:9): R$_f$=0.25; $^1$H NMR (400 MHz, DMSO) δ 8.47 (s, 1H), 8.02 (s, 1H), 7.82 (d, J=8.7 Hz, 2H), 7.41 (t, J=7.9 Hz, 2H), 7.16 (t, J=7.4 Hz, 1H), 7.05 (dd, J=8.1, 6.0 Hz, 4H), 5.00 (d, J=14.8 Hz, 1H), 4.93 (d, J=14.8 Hz, 1H), 4.42 (d, J=11.3 Hz, 1H), 4.24 (d, J=11.3 Hz, 1H), 1.63 (s, 3H); MS (ESI+): m\z 418.1390.

(R)-2-[(4-Pentyl-1H-1,2,3-triazol-1-yl)methyl]-2,3-dihydro-2-methyl-6-nitroimidazo[2,1-b]oxazole (I$_7$, Table 1, Scheme 3)

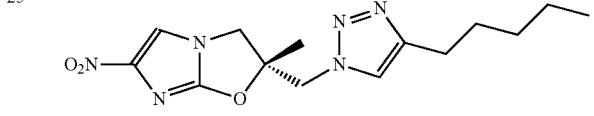

TLC (EtOAc:DCM 1:9): R$_f$=0.5; $^1$H NMR (400 MHz, Acetone) δ 8.18 (s, 1H), 7.80 (s, 1H), 4.62 (d, J=11.2 Hz, 2H), 4.40 (d, J=11.2 Hz, 2H), 2.25 (t, 2H), 1.75 (s, 3H), 1.21 (m, 4H), 1.15 (m, 2H), 0.91 (m, 3H); MS (ESI+): m\z 320.1579.

(R)-2-Methyl-6-nitro-2-((4-((4-(trifluoromethoxy)phenoxy)methyl)-1H-1,2,3-triazol-1-yl)methyl)-2,3-dihydroimidazo[2,1-b]oxazole (I$_8$, Table 1, Scheme 4)

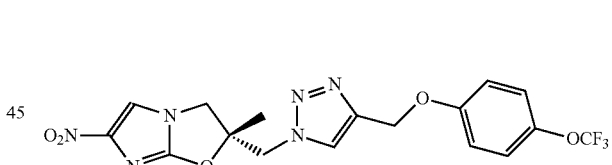

TLC (EtOAc:DCM 1:9): R$_f$=0.45; $^1$H NMR (400 MHz, Acetone) δ 8.18 (s, 1H), 7.79 (s, 1H), 7.28 (d, J=9.2 Hz, 2H), 7.14 (d, J=9.2 Hz, 2H), 5.22 (s, 2H), 5.08 (q, J=14.9 Hz, 2H), 4.65 (d, J=11.2 Hz, 1H), 4.42 (d, J=11.2 Hz, 1H), 1.78 (s, 3H); MS (ESI+): m\z 440.1056.

(R)-2-Methyl-6-nitro-2-((4-((4-(trifluoromethyl)phenoxy)methyl)-1H-1,2,3-triazol-1-yl)methyl)-2,3-dihydroimidazo[2,1-b]oxazole (I$_9$, Table 1, Scheme 4)

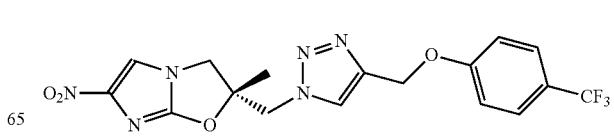

TLC (EtOAc:DCM 1:9): R$_f$=0.15; $^1$H NMR (400 MHz, DMSO) δ 8.23 (s, 1H), 8.05 (s, 1H), 7.65 (d, J=8.7 Hz, 2H), 7.20 (d, J=8.5 Hz, 2H), 5.23 (s, 2H), 4.97 (q, J=14.8 Hz, 2H), 4.39 (d, J=11.3 Hz, 1H), 4.23 (d, J=11.3 Hz, 1H), 1.59 (s, 3H); MS (ESI+): m\z 424.1107.

(R)-2-((4-((3-Chlorophenoxy)methyl)-1H-1,2,3-triazol-1-yl)methyl)-2-methyl-6-nitro-2,3-dihydroimidazo[2,1-b]oxazole (I$_{10}$, Table 1, Scheme 4)

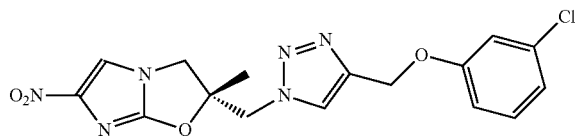 [SMILES: C[C@]1(Cn2cc(COc3cccc(Cl)c3)nn2)Cn2cc([N+](=O)[O-])nc2O1]

TLC (EtOAc:DCM 1:9): R$_f$=0.25; $^1$H NMR (400 MHz, DMSO) δ 8.21 (s, 1H), 8.05 (s, 1H), 7.30 (t, J=8.2 Hz, 1H), 7.11 (t, J=2.0 Hz, 1H), 6.99 (ddd, J=10.4, 8.2, 1.6 Hz, 2H), 5.14 (s, 2H), 4.96 (q, J=14.8 Hz, 2H), 4.39 (d, J=11.3 Hz, 1H), 4.22 (d, J=11.3 Hz, 1H), 1.59 (s, 3H); MS (ESI+): m\z 390.0843.

(R)-2-((4-((4-Bromophenoxy)methyl)-1H-1,2,3-triazol-1-yl)methyl)-2-methyl-6-nitro-2,3-dihydroimidazo[2,1-b]oxazole (I$_{11}$, Table 1, Scheme 4)

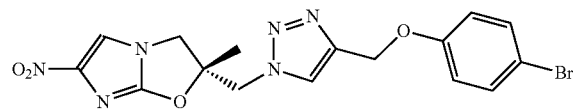 [SMILES: C[C@]1(Cn2cc(COc3ccc(Br)cc3)nn2)Cn2cc([N+](=O)[O-])nc2O1]

TLC (EtOAc:DCM 1:9): R$_f$=0.35; $^1$H NMR (400 MHz, DMSO) δ 8.20 (s, 1H), 8.04 (s, 1H), 7.44 (d, J=8.6 Hz, 2H), 6.98 (d, J=8.4 Hz, 2H), 5.11 (s, 2H), 4.96 (q, J=14.8 Hz, 2H), 4.38 (d, J=11.3 Hz, 1H), 4.22 (d, J=11.2 Hz, 1H), 1.58 (s, 3H); MS (ESI+): m\z 434.0338.

(R)-2-Methyl-6-nitro-2-((4-((p-tolyloxy)methyl)-1H-1,2,3-triazol-1-yl)methyl)-2,3-dihydroimidazo[2,1-b]oxazole (1$_{12}$, Table 1, Scheme 4)

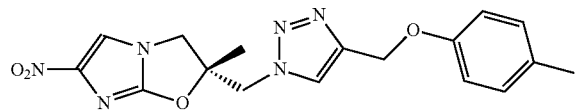 [SMILES: Cc1ccc(OCc2cn(C[C@@]3(C)Cn4cc([N+](=O)[O-])nc4O3)nn2)cc1]

TLC (EtOAc:DCM 1:9): R$_f$=0.3; $^1$H NMR (400 MHz, DMSO) δ 8.17 (s, 1H), 8.05 (s, 1H), 7.08 (d, J=8.2 Hz, 2H), 6.88 (d, J=8.4 Hz, 2H), 5.07 (s, 2H), 5.02-4.88 (m, 2H), 4.38 (d, J=11.3 Hz, 1H), 4.22 (d, J=11.3 Hz, 1H), 2.23 (s, 3H), 1.59 (s, 3H); MS (ESI+): m\z 370.1390.

(R)-2-Methyl-6-nitro-2-((4-((m-tolyloxy)methyl)-1H-1,2,3-triazol-1-yl)methyl)-2,3-dihydroimidazo[2,1-b]oxazole (I$_{13}$, Table 1, Scheme 4)

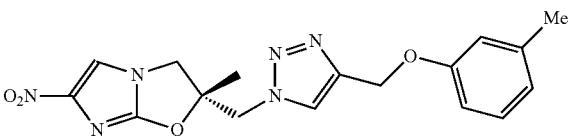 [SMILES: Cc1cccc(OCc2cn(C[C@@]3(C)Cn4cc([N+](=O)[O-])nc4O3)nn2)c1]

TLC (EtOAc:DCM 1:9): R$_f$=0.3; $^1$H NMR (400 MHz, DMSO) δ 8.17 (s, 1H), 8.03 (s, 1H), 7.15 (t, J=7.8 Hz, 1H), 6.77 (dd, J=16.5, 7.7 Hz, 3H), 5.07 (s, 2H), 4.95 (q, J=14.8 Hz, 2H), 4.38 (d, J=11.3 Hz, 1H), 4.22 (d, J=11.3 Hz, 1H), 2.26 (s, 3H), 1.58 (s, 3H); MS (ESI+): m\z 370.1390.

(R)-2-Methyl-6-nitro-2-((4-((o-tolyloxy)methyl)-1H-1,2,3-triazol-1-yl)methyl)-2,3-dihydroimidazo[2,1-b]oxazole (I$_{14}$, Table 1, Scheme 4)

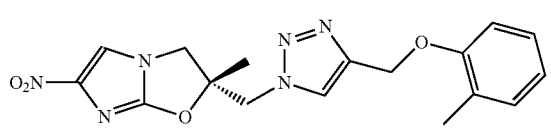 [SMILES: Cc1ccccc1OCc1cn(C[C@@]2(C)Cn3cc([N+](=O)[O-])nc3O2)nn1]

TLC (EtOAc:DCM 1:9): R$_f$=0.35; $^1$H NMR (400 MHz, Acetone) δ 8.14 (s, 7H), 7.78 (s, 6H), 7.12 (dt, J=22.2, 7.9 Hz, 26H), 6.85 (t, J=6.9 Hz, 8H), 5.17 (s, 21H), 5.07 (q, J=14.9 Hz, 27H), 4.62 (d, J=11.2 Hz, 12H), 4.40 (d, J=11.2 Hz, 12H), 2.13 (s, 20H), 1.77 (s, 36H); MS (ESI+): m\z 370.1390.

(R)-2-((4-((4-Ethylphenoxy)methyl)-1H-1,2,3-triazol-1-yl)methyl)-2-methyl-6-nitro-2,3-dihydroimidazo[2,1-b]oxazole (I$_{15}$, Table 1, Scheme 4)

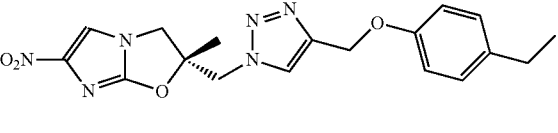 [SMILES: CCc1ccc(OCc2cn(C[C@@]3(C)Cn4cc([N+](=O)[O-])nc4O3)nn2)cc1]

TLC (EtOAc:DCM 1:9): R$_f$=0.5; $^1$H NMR (400 MHz, Acetone) δ 8.11 (s, 1H), 7.79 (s, 1H), 7.13 (d, J=8.4 Hz, 2H), 6.92 (d, J=8.5 Hz, 2H), 5.19-4.98 (m, 6H), 4.63 (d, J=11.2 Hz, 2H), 4.40 (d, J=11.1 Hz, 2H), 2.58 (dd, J=15.1, 7.5 Hz, 2H), 1.76 (s, 3H), 1.18 (t, J=7.6 Hz, 14H); MS (ESI+): m\z 384.1546.

(R)-2-((4-((3-Fluorophenoxy)methyl)-1H-1,2,3-triazol-1-yl)methyl)-2-methyl-6-nitro-2,3-dihydroimidazo[2,1-b]oxazole (I$_{16}$, Table 1, Scheme 4)

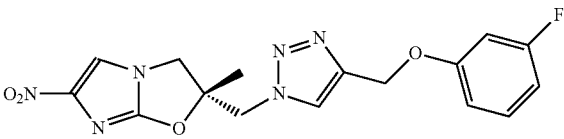 [SMILES: C[C@]1(Cn2cc(COc3cccc(F)c3)nn2)Cn2cc([N+](=O)[O-])nc2O1]

TLC (EtOAc:DCM 1:9): $R_f$=0.2; $^1$H NMR (400 MHz, DMSO) δ 8.21 (s, 1H), 8.03 (s, 1H), 7.30 (dd, J=15.3, 7.7 Hz, 1H), 6.93-6.72 (m, 3H), 5.12 (s, 2H), 4.96 (q, J=14.7 Hz, 2H), 4.38 (d, J=11.1 Hz, 1H), 4.22 (d, J=11.2 Hz, 1H), 1.59 (s, 3H); MS (ESI+): m\z 374.1139.

(R)-2-((4-((2-Fluorophenoxy)methyl)-1H-1,2,3-triazol-1-yl)methyl)-2-methyl-6-nitro-2,3-dihydroimidazo[2,1-b]oxazole (I$_{17}$, Table 1, Scheme 4)

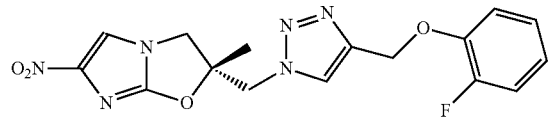 [SMILES: C[C@]1(Cn2cc(COc3ccccc3F)nn2)Cn2cc([N+](=O)[O-])nc2O1]

TLC (EtOAc:DCM 1:9): $R_f$=0.3; $^1$H NMR (400 MHz, Acetone) δ 8.18 (s, 1H), 7.80 (s, 1H), 7.29 (td, J=8.6, 1.6 Hz, 1H), 7.17-7.09 (m, 2H), 6.96 (ddd, J=7.8, 7.0, 1.5 Hz, 1H), 5.26 (s, 3H), 5.07 (q, J=14.9 Hz, 4H), 4.62 (d, J=11.2 Hz, 2H), 4.40 (d, J=11.2 Hz, 2H), 1.75 (s, 5H); MS (ESI+): m\z 374.1139.

(R)-2-((4-((4-Isopropylphenoxy)methyl)-1H-1,2,3-triazol-1-yl)methyl)-2-methyl-6-nitro-2,3-dihydroimidazo[2,1-b]oxazole (I$_{18}$, Table 1, Scheme 4)

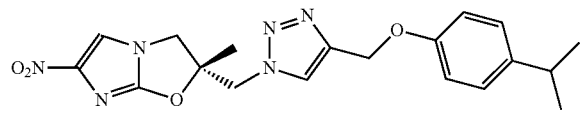 [SMILES: CC(C)c1ccc(OCc2cn(C[C@@]3(C)Cn4cc([N+](=O)[O-])nc4O3)nn2)cc1]

TLC (EtOAc:DCM 1:9): $R_f$=0.35; $^1$H NMR (400 MHz, DMSO) δ 8.18 (s, 1H), 8.07 (s, 1H), 7.14 (d, J=8.5 Hz, 2H), 6.91 (d, J=8.6 Hz, 2H), 5.07 (s, 2H), 4.96 (q, J=14.8 Hz, 2H), 4.39 (d, J=11.3 Hz, 1H), 4.22 (d, J=11.2 Hz, 1H), 2.83 (dt, J=13.8, 6.8 Hz, 1H), 1.58 (s, 3H), 1.17 (d, J=6.9 Hz, 6H); MS (ESI+): m\z 398.1703.

(R)-2-Methyl-6-nitro-2-((4-((pyridin-2-yloxy)methyl)-1H-1,2,3-triazol-1-yl)methyl)-2,3-dihydroimidazo[2,1-b]oxazole (I$_{19}$, Table 1, Scheme 5)

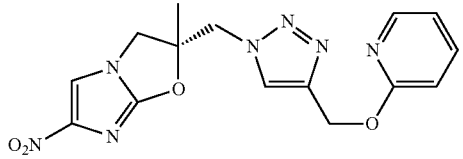 [SMILES: C[C@]1(Cn2cc(COc3ccccn3)nn2)Cn2cc([N+](=O)[O-])nc2O1]

TLC (EtOAc:DCM 1:9): $R_f$=0.4; $^1$H NMR (400 MHz, DMSO) δ 8.19 (s, 1H), 8.04 (s, 1H), 7.98 (m, 1H), 7.25-7.38 (m, 3H), 5.10 (s, 2H), 4.95 (q, J=14.8 Hz, 2H), 4.38 (d, J=11.3 Hz, 1H), 4.22 (d, J=11.2 Hz, 1H), 1.58 (s, 3H); MS (ESI+): m\z 357.1186.

(R)-2-Methyl-6-nitro-2-((4-((p-tolylthio)methyl)-1H-1,2,3-triazol-1-yl)methyl)-2,3-dihydroimidazo[2,1-b]oxazole (I$_{20}$, Table 1, Scheme 5)

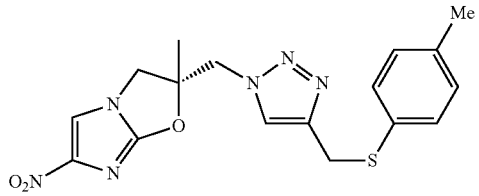 [SMILES: Cc1ccc(SCc2cn(C[C@@]3(C)Cn4cc([N+](=O)[O-])nc4O3)nn2)cc1]

TLC (EtOAc:DCM 1:9): $R_f$=0.3; $^1$H NMR (400 MHz, DMSO) δ 8.17 (s, 1H), 8.05 (s, 1H), 7.08 (d, J=8.2 Hz, 2H), 6.88 (d, J=8.4 Hz, 2H), 5.07 (s, 2H), 5.02-4.88 (m, 2H), 4.38 (d, J=11.3 Hz, 1H), 4.22 (d, J=11.3 Hz, 1H), 2.23 (s, 3H), 1.59 (s, 3H); MS (ESI+): m\z 386.1161.

(R)-2-Methyl-6-nitro-2-((4-(2-(p-tolyloxy)ethyl)-1H-1,2,3-triazol-1-yl)methyl)-2,3-dihydroimidazo[2,1-b]oxazole (I$_{21}$, Table 1, Scheme 5)

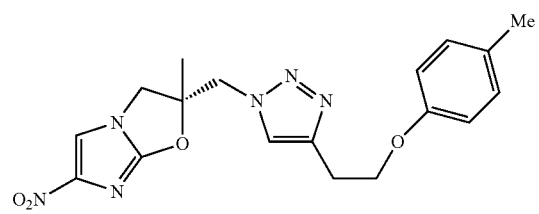 [SMILES: Cc1ccc(OCCc2cn(C[C@@]3(C)Cn4cc([N+](=O)[O-])nc4O3)nn2)cc1]

TLC (EtOAc:DCM 1:9): $R_f$=0.35; $^1$H NMR (400 MHz, DMSO) δ 8.17 (s, 1H), 8.05 (s, 1H), 7.08 (d, J=8.2 Hz, 2H), 6.88 (d, J=8.4 Hz, 2H), 5.02-4.88 (m, 2H), 4.38 (d, J=11.3 Hz, 1H), 4.22 (d, J=11.3 Hz, 1H), 4.12 (d, J=4.8 Hz, 2H), 2.32 (d, J=4.8 Hz, 2H), 2.23 (s, 3H), 1.59 (s, 3H); MS (ESI+): m\z 384.1546.

(R)-2-Methyl-2-((4-(morpholinomethyl)-1H-1,2,3-triazol-1-yl)methyl)-6-nitro-2,3-dihydroimidazo[2,1-b]oxazole (I$_{22}$, Table 1, Scheme 5)

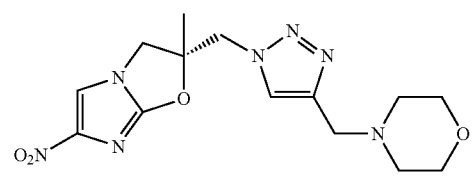 [SMILES: C[C@]1(Cn2cc(CN3CCOCC3)nn2)Cn2cc([N+](=O)[O-])nc2O1]

TLC (EtOAc:DCM 1:9): $R_f$=0.25; $^1$H NMR (400 MHz, DMSO) δ 8.16 (s, 1H), 8.06 (s, 1H), 5.04 (s, 2H), 5.02-4.88 (m, 2H), 4.38 (d, J=11.3 Hz, 1H), 4.22 (d, J=11.3 Hz, 1H), 4.09-4.18 (d, 4H), 3.36-3.48 (m, 4H), 1.58 (s, 3H); MS (ESI+): m\z 349.1499.

Biological Evaluation

Example 1

In Vitro Activity of Compounds I$_1$ to I$_{22}$ Against *M. tuberculosis* H$_{37}$Rv and Two Clinical Isolates (*M. tuberculosis* MDR & *M. tuberculosis* XDR)

MIC Determination:

MIC was determined by broth dilution method against *M. tuberculosis* $H_{37}Rv$ (ATCC 27294; American Type Culture Collection, Manassas, Va.), *M. tuberculosis* MDR (resistant to isoniazid and rifampicin) and *M. tuberculosis* XDR (resistant to isoniazid, rifampicin, amikacin and moxifloxacin). The bacterial strains were grown for 10 to 15 days in Middlebrook 7H9 broth (Difco Laboratories, Detroit, Mich.) supplemented with 0.5% (v/v) glycerol, 0.25% (v/v) Tween 80 (Himedia, Mumbai India), and 10% ADC (albumin dextrose catalase, Becton Dickinson, Sparks, Md.) under shaking conditions at 37° C. in 5% $CO_2$ to facilitate exponential-phase growth of the organism. Bacterial suspension was prepared by suspending *M. tuberculosis* growth in normal saline containing 0.5% tween 80 and turbidity was adjusted to 1 McFarland standard which is equivalent to $1.5 \times 10^7$ CFU/ml. The 2-fold serial dilutions of compounds $I_1$ to $I_{22}$ were prepared in Middle brook 7H9 (Difco laboratories) for *M. tuberculosis* in 100 μl per well in 96-well U bottom microtitre plates (Tarson, Mumbai, India). The above-mentioned bacterial suspension was further diluted in the growth media and 100 μl volume of this diluted inoculum was added to each well of the plate resulting in the final inoculum of $5 \times 10^5$ CFU/ml in the well and the final concentrations of compound $I_1$ to $I_{22}$ ranged from 0.015 to 32 μg/ml (0.015, 0.03, 0.06, 0.12, 0.25, 0.5, 1, 2, 4, 8, 16, 32). The plates were incubated at 37° C. for 3-weeks in 5% $CO_2$. The plates were read visually and the minimum concentration of the compound showing no turbidity was recorded as MIC.

Results:

i) The compounds of general formula I (compounds $I_1$ to $I_{22}$), were screened against both replicating & non-replicating stages of *M. tuberculosis*, wherein 7 compounds $I_{10}$, $I_{11}$, $I_{13}$, $I_{14}$, $I_{17}$, $I_{18}$ and $I_{21}$ showed MIC value of <1.0 μg/ml (results provided in Table 2). Three compounds $I_{11}$, $I_{17}$ and $I_{21}$ showed very potent MIC of 0.12, 0.25 and 0.25 μg/ml against replicating stages of *M. Tuberculosis* and MIC of 0.25, 0.5 and 0.25 against non-replicating stages of *M. Tuberculosis*. The results are given in Table 2.

ii) The compounds of general formula I (compounds $I_1$ to $I_{22}$), were screened against both multi-drug and extensive-drug resistant strains of *M. tuberculosis*, wherein five compounds $I_{11}$, $I_{17}$, $I_{19}$, $I_{20}$ and $I_{21}$ showed MIC value of <1.0 μg/ml. Three compounds $I_{11}$, $I_{17}$ and $I_{21}$ showed very potent MIC of 0.12, 0.5 and 0.25 μg/ml against multi and extensive-drug resistant strains of *M. Tuberculosis*. The results are given in Table 2.

Example 2

Cytotoxicity Assay of Compounds $I_1$ to $I_{22}$:

Cell Culture:

The study was carried out using macrophage J774 cells line (ATCC-USA). Cells were grown in Rosewell Park Memorial Institute Medium (RPMI) containing 10% fetal calf serum (FCS) and supplemented with 75 mg/liter penicillin, 100 mg/liter streptomycin, 110 mg/liter Sodium pyruvate, 2.38 gm/liter HEPES, 0.05 mM 2 β-mercaptoethanol, and 2 gm/liter $NaHCO_3$, in a humidified atmosphere in 5% $CO_2$ at 37° C., and were sub-cultured at 1:4 ratio once a week.

Cell Treatment:

Cells were plated at a density of $3 \times 10^4$ cells/cm$^2$ and maintained in culture medium for 12 hours. Cells were seeded onto 96-well flat bottom plates and FCS was reduced to 5% for the experiment. Stock solutions of compounds 9 to 37 were prepared fresh to avoid oxidation. Cells were incubated with the compounds (40 μg/ml) for 24 hrs.

Cytotoxicity Assays:

After the completion of incubation, the medium was removed and cell viability was evaluated by assaying for the ability of functional mitochondria to catalyze the reduction of 3-(4,5-dimethylthiazol-2-yl)-2,5-diphenyltetrazolium bromide (MTT) to form formazan salt by mitochondrial dehydrogenases, and determined by Elisa reader at 450 nm (Multiskan Spectrum; Thermo Electron Corporation, USA). Percentage cytotoxicity was calculated with respect to the untreated cells.

Results:

Compounds $I_1$ to $I_{22}$ were not toxic up to 40 μg/ml concentration and the cytotoxicity assay results are shown in Table 2.

TABLE 1

Structure of representative compounds $I_1$ to $I_{22}$ of general formula I

| Entries | Codes | Structures |
|---|---|---|
| 1 | $I_1$ | 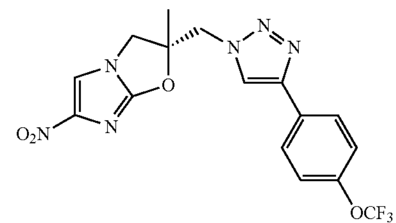 [SMILES: C[C@]1(Cn2cc(-c3ccc(OC(F)(F)F)cc3)nn2)Cn2cc([N+](=O)[O-])nc2O1] |
| 2 | $I_2$ | 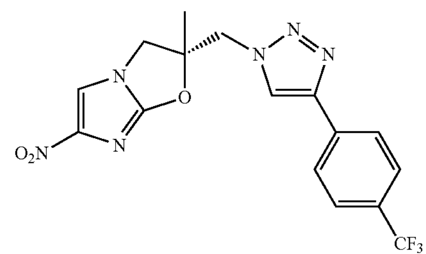 [SMILES: C[C@]1(Cn2cc(-c3ccc(C(F)(F)F)cc3)nn2)Cn2cc([N+](=O)[O-])nc2O1] |
| 3 | $I_3$ | 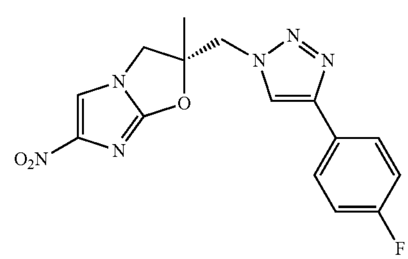 [SMILES: C[C@]1(Cn2cc(-c3ccc(F)cc3)nn2)Cn2cc([N+](=O)[O-])nc2O1] |
| 4 | $I_4$ | 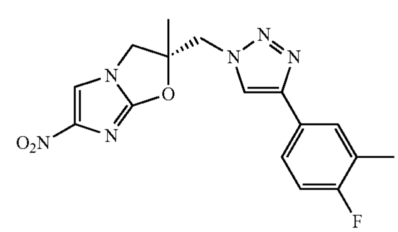 [SMILES: Cc1cc(-c2cn(C[C@@]3(C)Cn4cc([N+](=O)[O-])nc4O3)nn2)ccc1F] |

TABLE 1-continued

Structure of representative compounds I₁ to I₂₂ of general formula I

| Entries | Codes | Structures |
|---|---|---|
| 5 | I₅ | |
| 6 | I₆ | |
| 7 | I₇ | |
| 8 | I₈ | |
| 9 | I₉ | |
| 10 | I₁₀ | |
| 11 | I₁₁ | |
| 12 | I₁₂ | |
| 13 | I₁₃ | 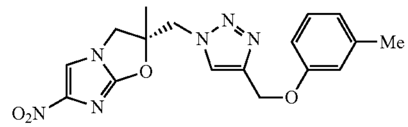 [SMILES: Cc1cccc(OCc2cn(C[C@@]3(C)Cn4cc([N+](=O)[O-])nc4O3)nn2)c1] |
| 14 | I₁₄ | 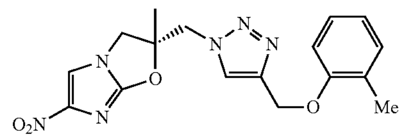 [SMILES: Cc1ccccc1OCc1cn(C[C@@]2(C)Cn3cc([N+](=O)[O-])nc3O2)nn1] |
| 15 | I₁₅ | 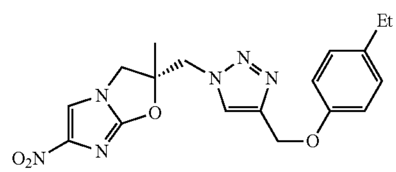 |
| 16 | I₁₆ | 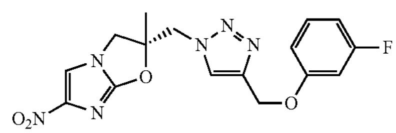 [SMILES: C[C@]1(Cn2cc(COc3cccc(F)c3)nn2)Cn2cc([N+](=O)[O-])nc2O1] |
| 17 | I₁₇ | 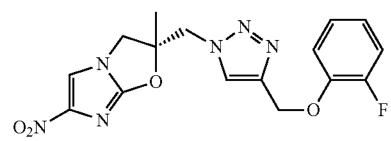 [SMILES: C[C@]1(Cn2cc(COc3ccccc3F)nn2)Cn2cc([N+](=O)[O-])nc2O1] |
| 18 | I₁₈ | 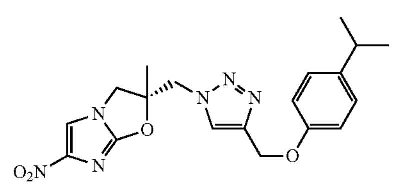 [SMILES: CC(C)c1ccc(OCc2cn(C[C@@]3(C)Cn4cc([N+](=O)[O-])nc4O3)nn2)cc1] |
| 19 | I₁₉ | 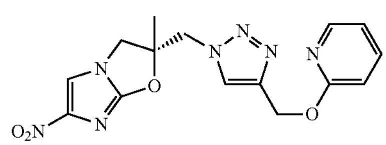 [SMILES: C[C@]1(Cn2cc(COc3ccccn3)nn2)Cn2cc([N+](=O)[O-])nc2O1] |
| 20 | I₂₀ | 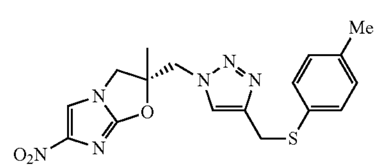 [SMILES: Cc1ccc(SCc2cn(C[C@@]3(C)Cn4cc([N+](=O)[O-])nc4O3)nn2)cc1] |
| 21 | I₂₁ | 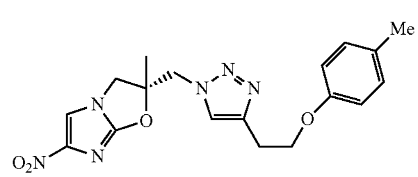 [SMILES: Cc1ccc(OCCc2cn(C[C@@]3(C)Cn4cc([N+](=O)[O-])nc4O3)nn2)cc1] |

TABLE 1-continued

Structure of representative compounds
$I_1$ to $I_{22}$ of general formula I

| Entries | Codes | Structures |
|---|---|---|
| 22 | $I_{22}$ | 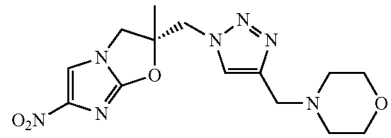 [SMILES: C[C@]1(Cn2cc(CN3CCOCC3)nn2)Cn2cc([N+](=O)[O-])nc2O1] |

TABLE 2

Anti-tuberculosis activity and cytotoxicity of representative compounds of general formula I ($I_1$ to $I_{22}$)

| | | MIC(μg/ml) | | | | | |
|---|---|---|---|---|---|---|---|
| S. No. | Compound code | M. tb $H_{37}Rv$ | Non-replicating strain | MIC ($Rif^R$) | MDR | XDR | Cytotoxicity (μg/ml) |
| 1. | $I_1$ | 2 | 4 | 2 | 2 | 1 | >40 |
| 2. | $I_2$ | 2 | 8 | 4 | 2 | 2 | >40 |
| 3. | $I_3$ | 1 | 2 | 2 | 2 | 2 | >40 |
| 4. | $I_4$ | 2 | 4 | 1 | 4 | 2 | >40 |
| 5. | $I_5$ | 1 | 8 | 4 | 1 | 4 | >40 |
| 6. | $I_6$ | 2 | 2 | 1 | 1 | 1 | >40 |
| 7. | $I_7$ | 2 | 4 | 8 | 2 | 8 | >40 |
| 8. | $I_8$ | 2 | 4 | 2 | 2 | 2 | >40 |
| 9. | $I_9$ | 1 | 2 | 4 | 4 | 4 | >40 |
| 10. | $I_{10}$ | 0.5 | 1 | 2 | 2 | 4 | >40 |
| 11. | $I_{11}$ | 0.12 | 0.25 | 0.12 | 0.12 | 0.25 | >40 |
| 12. | $I_{12}$ | 1 | 2 | 8 | 2 | 8 | >40 |
| 13. | $I_{13}$ | 0.5 | 0.5 | 1 | 1 | 2 | >40 |
| 14. | $I_{14}$ | 0.5 | 2 | 1 | 1 | 1 | >40 |
| 15. | $I_{15}$ | 2 | 2 | 4 | 2 | 4 | >40 |
| 16. | $I_{16}$ | 1 | 2 | 2 | 2 | 2 | >40 |
| 17. | $I_{17}$ | 0.25 | 0.5 | 1 | 0.5 | 1 | >40 |
| 18. | $I_{18}$ | 0.5 | 1 | 2 | 1 | 4 | >40 |
| 19. | $I_{19}$ | 1 | 2 | 0.5 | 0.25 | 0.5 | >40 |
| 20. | $I_{20}$ | 2 | 1 | 0.25 | 0.5 | 2 | >40 |
| 21. | $I_{21}$ | 0.25 | 0.25 | 1 | 0.25 | 0.25 | >40 |
| 22. | $I_{22}$ | 2 | 1 | 2 | 2 | 2 | >40 |

We claim:

1. A compound of general formula I,

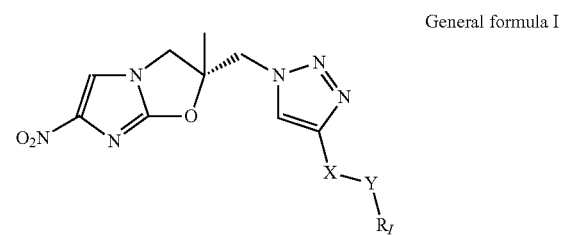

General formula I wherein
'X' is selected from a group $(CH_2)_n$ or a direct bond, where n is any number from 0, 1, 2 to 6,
'Y' is selected from a group O, S or direct bond,
$R_I$ is selected from the group consisting of H, alkyl, substituted alkyl, aryl, substituted aryl, biaryl, substituted biaryl, heterocyclic and substituted heterocyclic, wherein the substituted heterocyclic is selected from any of the following rings consisting of piperazinyl, morpholinyl, piperidyl, pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl and the substitution on aryl and biaryl is selected from the group consisting of F, Cl, Br, I, $CF_3$, $OCF_3$, $OR_{f1}$, $NO_2$ and alkyl chain from C1 to C14,
wherein $R_{f1}$ is selected from the group consisting of H, alkyl, phenyl and substituted phenyl.

2. The compound of formula I as claimed in claim 1, wherein the compound is selected from the group consisting of the following compounds:
(R)-2-{[4-(4-trifluoromethoxyphenyl)-1H-1,2,3-triazol-1-yl]methyl}-2,3-dihydro-2-methyl-6-nitroimidazo[2,1-b]oxazole (compound $I_1$),
(R)-2-{[4-(4-trifluoromethylphenyl)-1H-1,2,3-triazol-1-yl]methyl}-2,3-dihydro-2-methyl-6-nitroimidazo[2,1-b]oxazole (compound $I_2$),
(R)-2-{[4-(4-fluorophenyl)-1H-1,2,3-triazol-1-yl]methyl}-2,3-dihydro-2-methyl-6-nitroimidazo[2,1-b]oxazole (compound $I_3$),
(R)-2-{[4-(4-fluoro-3-methylphenyl)-1H-1,2,3-triazol-1-yl]methyl}-2,3-dihydro-2-methyl-6-nitroimidazo[2,1-b]oxazole (compound $I_4$),
(R)-2-{[4-(2,4-difluorophenyl)-1H-1,2,3-triazol-1-yl]methyl}-2,3-dihydro-2-methyl-6-nitroimidazo[2,1-b]oxazole (compound $I_5$),
(R)-2-{[4-(4-phenoxyphenyl)-1H-1,2,3-triazol-1-yl]methyl}-2,3-dihydro-2-methyl-6-nitroimidazo[2,1-b]oxazole (compound $I_6$),
(R)-2-[(4-pentyl-1H-1,2,3-triazol-1-yl)methyl]-2,3-dihydro-2-methyl-6-nitroimidazo[2,1-b]oxazole (compound $I_7$),
(R)-2-{[4-(4-trifluoromethoxyphenoxy)methyl)-1H-1,2,3-triazol-1-yl]methyl}-2,3-dihydro-2-methyl-6-nitroimidazo[2,1-b]oxazole (compound $I_8$),
(R)-2-{[4-(4-trifluoromethylphenoxy)methyl)-1H-1,2,3-triazol-1-yl]methyl}-2,3-dihydro-2-methyl-6-nitroimidazo[2,1-b]oxazole (compound $I_9$),
(R)-2-{[4-(3-chlorophenoxy)methyl)-1H-1,2,3-triazol-1-yl]methyl}-2,3-dihydro-2-methyl-6-nitroimidazo[2,1-b]oxazole (compound $I_{10}$),
(R)-2-{[4-(4-bromophenoxy)methyl)-1H-1,2,3-triazol-1-yl]methyl}-2,3-dihydro-2-methyl-6-nitroimidazo[2,1-b]oxazole (compound $I_{11}$),
(R)-2-{[4-(4-methylphenoxy)methyl)-1H-1,2,3-triazol-1-yl]methyl}-2,3-dihydro-2-methyl-6-nitroimidazo[2,1-b]oxazole (compound $I_{12}$),
(R)-2-{[4-(3-methylphenoxy)methyl)-1H-1,2,3-triazol-1-yl]methyl}-2,3-dihydro-2-methyl-6-nitroimidazo[2,1-b]oxazole (compound $I_{13}$),
(R)-2-{[4-(2-methylphenoxy)methyl)-1H-1,2,3-triazol-1-yl]methyl}-2,3-dihydro-2-methyl-6-nitroimidazo[2,1-b]oxazole (compound $I_{14}$),
(R)-2-{[4-(4-ethylphenoxy)methyl)-1H-1,2,3-triazol-1-yl]methyl}-2,3-dihydro-2-methyl-6-nitroimidazo[2,1-b]oxazole (compound $I_{15}$),
(R)-2-{[4-(3-fluorophenoxy)methyl)-1H-1,2,3-triazol-1-yl]methyl}-2,3-dihydro-2-methyl-6-nitroimidazo[2,1-b]oxazole (compound $I_{16}$),
(R)-2-{[4-(2-fluorophenoxy)methyl)-1H-1,2,3-triazol-1-yl]methyl}-2,3-dihydro-2-methyl-6-nitroimidazo[2,1-b]oxazole (compound $I_{17}$),
(R)-2-{[4-(4-isopropylphenoxy)methyl)-1H-1,2,3-triazol-1-yl]methyl}-2,3-dihydro-2-methyl-6-nitroimidazo[2,1-b]oxazole (compound $I_{18}$),
(R)-2-methyl-6-nitro-2-((4-((pyridin-2-yloxy)methyl)-1H-1,2,3-triazol-1-yl)methyl)-2,3-dihydroimidazo[2,1-b]oxazole (compound $I_{19}$), (R)-2-methyl-6-nitro-2-((4-((p-tolylthio)methyl)-1H-1,2,3-triazol-1-yl)methyl)-2,3-dihydroimidazo[2,1-b]oxazole (compound I₂₀), (R)-2-methyl-6-nitro-2-((4-(2-(p-tolyloxy)ethyl)-1H-1,2,3-triazol-1-yl)methyl)-2,3-dihydroimidazo[2,1-b]oxazole (compound I₂₁) and (R)-2-methyl-2-((4-(morpholinomethyl)-1H-1,2,3-triazol-1-yl)methyl)-6-nitro-2,3-dihydroimidazo[2,1-b]oxazole (compound I₂₂).

3. The compound of general formula I as claimed in claim 1, for use in the treatment of tuberculosis.

4. The compound of formula I as claimed in claim 1, wherein said compound exhibits an in vitro anti-tuberculosis activity against replicating and non-replicating stages of *Mycobacterium tuberculosis* with MIC values in the range of 0.12 to 32 μg/ml.

5. The compound of formula I as claimed in claim 1, wherein said compound exhibits an in vitro anti-tuberculosis activity against XDR *Mycobacterium tuberculosis* (resistant to isoniazid, rifampicin, amikacin and moxifloxacin), MDR-TB (resistant to isoniazid and rifampicin) with MIC values in the range of 0.12 to 32 μg/ml and the compound does not exhibit any cytotoxicity up to 40 μg/ml in macrophage J774 cell line.

6. The compound of formula I as claimed in claim 2, wherein said compound exhibits an in vitro anti-tuberculosis activity against replicating and non-replicating stages of *Mycobacterium tuberculosis* with MIC values in the range of 0.12 to 32 μg/ml.

7. The compound of formula I as claimed in claim 2, wherein said compound exhibits an in vitro anti-tuberculosis activity against XDR *Mycobacterium tuberculosis* (resistant to isoniazid, rifampicin, amikacin and moxifloxacin), MDR-TB (resistant to isoniazid and rifampicin) with MIC values in the range of 0.12 to 32 μg/ml and the compound does not exhibit any cytotoxicity up to 40 μg/ml in macrophage J774 cell line.

8. A process for preparation of the compound of formula I as claimed in claim 2 wherein the said process comprising the steps:

i) reacting a compound of formula 8 in an organic solvent and in the presence of an azide source at a temperature in the range of 25° C. to 80° C. for a period ranging between 1 h to 3 h to obtain a compound of formula 9;

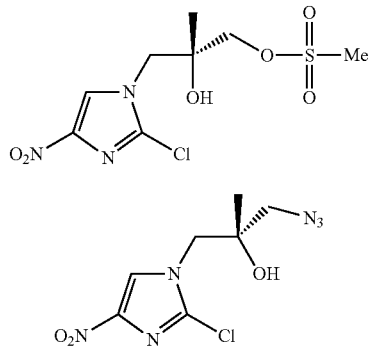

ii) reacting the compound of formula 9 in an organic solvent and in the presence of a base at a temperature in the range of 10° C.-25° C. for a period of 1 h to 12 h to obtain a compound of formula 10;

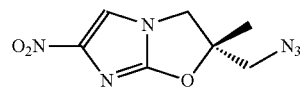

iii) reacting the compound of formula 10 with a compound of formula selected from the group consisting of formula 13 (a-k) or 14 (a-g) or 15 (a-d) in 1:1 tert-BuOH/H₂O mixture in the presence of sodium ascorbate and CuSO₄ at a temperature in the range of 10° C. to 25° C. for a period of 1 h to 12 h to obtain the compound of formula I

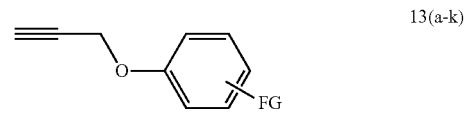

13a; FG = 4-OCF₃
13b; FG = 4-CF₃
13c; FG = 4-Cl
13d; FG = 2-Br
13e; FG = 4-Me
13f; FG = 3-Me
13g; FG = 2-Me
13h; FG = 4-Et
13i; FG = 3-F
13j; FG = 2-F
13k; FG = 4-iso-propyl

14a; R = 4-OCF₃ Ph
14b; R = 4-CF₃ Ph
14c; R = 4-F Ph
14d; R = 4-F, 3-Me Ph
14e; R = 2,4-difluoro Ph
14f; R = 4-phenoxy Ph
14g; R = n-pentyl

15a; n = 1, R = 2-pyridyl
15b; n = 1, R = 4-Me thiophenoxyl
15c; n = 2, R = 4-Me phenoxyl
15d; n = 1, R = morpholinyl 9. The process as claimed in claim 8, wherein the organic solvent in step i) is selected from toluene, acetonitrile, DMF, dichloroethane or any combination thereof.

10. The process as claimed in claim 8, wherein the azide source in step i) is selected from sodium azide, trimethylsilylazide, tetrabutyl ammonium bromide or any combination thereof.

11. The process as claimed in claim 8, wherein the base in step ii) is selected from sodium hydride, cesium carbonate, potassium carbonate or any combination thereof.

12. The process as claimed in claim 8, wherein the organic solvent in step ii) is selected from toluene, acetonitrile, DMF, tetrahydrofuran or any combination thereof.

* * * * *